United States Patent
Cohen et al.

(10) Patent No.: US 10,035,802 B2
(45) Date of Patent: Jul. 31, 2018

(54) SOLID STATE FORMS OF IBRUTINIB

(71) Applicant: ASSIA CHEMICAL INDUSTRIES LTD., Petach Tikva (IL)

(72) Inventors: Meital Cohen, Pethah-tikva (IL); Yuval Cohen, Rishon Lezion (IL); Ariel Mittelman, Elad (IL); Elana Ben Moha-Lerman, Ono (IL); Idit Tzanani, Kfar Saba (IL); Leonid Levenfeld, Petach Tikva (IL)

(73) Assignee: TEVA PHARMACEUTICALS USA, INC., North Wales, PA (US)

( * ) Notice: Subject to any disclaimer, the term of this patent is extended or adjusted under 35 U.S.C. 154(b) by 0 days.

(21) Appl. No.: 15/503,450

(22) PCT Filed: Aug. 13, 2015

(86) PCT No.: PCT/US2015/045070
§ 371 (c)(1),
(2) Date: Feb. 13, 2017

(87) PCT Pub. No.: WO2016/025720
PCT Pub. Date: Feb. 18, 2016

(65) Prior Publication Data

US 2017/0226114 A1    Aug. 10, 2017

Related U.S. Application Data (60) Provisional application No. 62/037,366, filed on Aug. 14, 2014, provisional application No. 62/130,828, filed on Mar. 10, 2015.

(51) Int. Cl.
*A01N 43/90* (2006.01)
*A61K 31/519* (2006.01)
*C07D 487/04* (2006.01)

(52) U.S. Cl.
CPC .......... *C07D 487/04* (2013.01); *A61K 31/519* (2013.01); *C07B 2200/13* (2013.01)

(58) Field of Classification Search
CPC ........................... A61K 31/519; C07D 487/04
USPC ....................................... 514/262.1; 544/262
See application file for complete search history.

(56) References Cited

FOREIGN PATENT DOCUMENTS

| CN | 103 923 084 A | 7/2014 |
|---|---|---|
| WO | WO 2013/184572 | 12/2013 |
| WO | WO 2015/081180 | 6/2015 |

*Primary Examiner* — Jeffrey H Murray
(74) *Attorney, Agent, or Firm* — Chalin A. Smith; Smith Patent, LLC (57) ABSTRACT

The present invention encompasses solid state forms of Ibrutinib, including forms G, J and K, and pharmaceutical compositions thereof.

14 Claims, 5 Drawing Sheets

Figure 1: A characteristic X-ray powder diffractogram of form G of Ibrutinib.

Figure 2: A characteristic X-ray powder diffractogram of form J of Ibrutinib.

Figure 3: A characteristic DSC thermogram of form G.

Figure 4: A characteristic TGA thermogram of form G.

Figure 5: A characteristic X-ray powder diffractogram of form K of Ibrutinib.

SOLID STATE FORMS OF IBRUTINIB

CROSS REFERENCE TO RELATED APPLICATION

This application is a National Stage application of PCT/US2015/045070, filed Aug. 13, 2015, which claims the benefit of U.S. Provisional Application Nos. 62/037,366, filed Aug. 14, 2014; and 62/130,828, filed Mar. 10, 2015, the entire disclosures of which are incorporated by reference herein for all purposes.

FIELD OF THE INVENTION

The present invention encompasses solid state forms of Ibrutinib and pharmaceutical compositions thereof.

BACKGROUND OF THE INVENTION

Ibrutinib, 1-{(3R)-3-[4-amino-3-(4-phenoxyphenyl)-1H-pyrazolo[3,4-d]pyrimidin-1-yl]piperidin-1-yl]prop-2-en-1-one, having the following formula, is a kinase inhibitor indicated for the treatment of patients with B-cell lymphoma. Ibrutinib is described in U.S. Pat. No. 7,514,444 and in U.S. Pat. No. 8,008,309. Solid state forms, including forms A-F and amorphous form of Ibrutinib, are described in WO 2013/184572.

Polymorphism, the occurrence of different crystalline forms, is a property of some molecules and molecular complexes. A single molecule may give rise to a variety of polymorphs having distinct crystal structures and physical properties like melting point, thermal behaviors (e.g. measured by thermogravimetric analysis—"TGA", or differential scanning calorimetry—"DSC"), X-ray diffraction pattern, infrared absorption fingerprint, and solid state ($^{13}$C-) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, changing the dissolution profile in a favorable direction, or improving stability (polymorph as well as chemical stability) and shelf-life. These variations in the properties of different salts and solid state forms may also offer improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to assess variations in the properties and characteristics of a solid active pharmaceutical ingredient.

Discovering new solid state forms and solvates of a pharmaceutical product may yield materials having desirable processing properties, such as ease of handling, ease of processing, storage stability, and ease of purification, or may serve as desirable intermediate crystal forms that facilitate purification or conversion to other polymorphic forms. New solid state forms of a pharmaceutically useful compound can also provide an opportunity to improve the performance characteristics of a pharmaceutical product. It enlarges the repertoire of materials that a formulation scientist has available for formulation optimization, for example by providing a product with different properties, e.g., a different crystal habit, higher crystallinity or polymorphic stability which may offer better processing or handling characteristics, improved dissolution profile, or improved shelf-life (chemical/physical stability). For at least these reasons, there is a need for additional solid state forms (including solvated forms) of Ibrutinib.

SUMMARY OF THE INVENTION

The present invention provides novel solid state forms of Ibrutinib, and pharmaceutical compositions comprising said Ibrutinib solid state forms.

The present invention also encompasses the use of the Ibrutinib solid state forms of the present invention for the preparation of pharmaceutical compositions and/or formulations of Ibrutinib. The present invention also comprises a process for preparing the above mentioned pharmaceutical formulations. The process comprises combining the Ibrutinib solid state form or pharmaceutical compositions comprising the Ibrutinib solid state form with at least one pharmaceutically acceptable excipient.

The solid state forms of Ibrutinib, the pharmaceutical compositions or the pharmaceutical formulations comprising the solid state forms of Ibrutinib according to the present invention can be used as medicaments, particularly for the treatment of cancer.

The present invention also provides a method of treating cancer, comprising administering a therapeutically effective amount of the Ibrutinib solid state forms of the present invention, or at least one of the above pharmaceutical compositions or pharmaceutical formulations, to a subject suffering from cancer, or otherwise in need of the treatment.

The present invention further provides the use of Ibrutinib in the preparation of other solid state forms of Ibrutinib or Ibrutinib salts and solid state forms thereof.

DETAILED DESCRIPTION OF THE INVENTION

The present invention encompasses solid state forms of Ibrutinib. Solid state properties of Ibrutinib can be influenced by controlling the conditions under which the Ibrutinib is obtained in solid form.

In some embodiments, the crystalline form of Ibrutinib of the invention is substantially free of any other forms of Ibrutinib, or of specified polymorphic forms of Ibrutinib, respectively.

As used herein, "substantially free" means that the solid state forms of the present invention contain 20% (w/w) or less of other polymorphs, or, alternatively, of a specified polymorph of Ibrutinib. According to some embodiments, the solid state forms of the present invention contain 10% (w/w) or less, 5% (w/w) or less, 2% (w/w) or less of other polymorphs, or of a specified polymorph of Ibrutinib. In other embodiments, solid state forms of Ibrutinib of the present invention contain from 1% to 20% (w/w), from 5% to 20% (w/w), or from 5% to 10% (w/w) of other solid state forms, or of a specified polymorph of Ibrutinib.

Depending on which other solid state forms comparison is made with, the crystalline forms of Ibrutinib of the present invention have advantageous properties selected from at least one of the following: chemical purity, solubility, dissolution rate, morphology or crystal habit, stability (such as chemical stability as well as thermal and mechanical stability with respect to polymorphic conversion, or stability towards dehydration and/or storage stability), low content of residual solvent, a lower degree of hygroscopicity, or advantageous processing and handling characteristics such as flowability, compressibility, and bulk density.

A solid state form, such as a crystal form or amorphous form, may be referred to herein as being characterized by graphical data "as depicted in" or "as substantially depicted in" a Figure. Such data include, for example, powder X-ray diffractograms and solid state NMR spectra. As is well-known in the art, the graphical data potentially provides additional technical information to further define the respective solid state form (a so-called "fingerprint") which cannot necessarily be described by reference to numerical values or peak positions alone. In any event, the skilled person will understand that such graphical representations of data may be subject to small variations, e.g., in peak relative intensities and peak positions due to certain factors such as, but not limited to, variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of a Ibrutinib referred to herein as being characterized by graphical data "as depicted in" or "as substantially depicted in" a Figure will thus be understood to include any crystal forms of Ibrutinib characterized with the graphical data having such small variations, as is well known to the skilled person, in comparison with the Figure.

As used herein, the term "isolated" in reference to solid state forms of Ibrutinib of the present invention corresponds to a solid state form of Ibrutinib that is physically separated from the reaction mixture in which it is formed.

As used herein, unless stated otherwise, the XRPD measurements are taken using copper Kα radiation wavelength 1.5418 Å.

A thing, e.g., a reaction mixture, may be characterized herein as being at, or allowed to come to "room temperature" or "ambient temperature", often abbreviated as "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

The amount of solvent employed in a chemical process, e.g., a reaction or crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending a 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding solvent X (1.5 v/v) to a 100 ml reaction mixture would indicate that 150 mL of solvent X was added.

A process or step may be referred to herein as being carried out "overnight." This refers to a time interval, e.g., for the process or step, that spans the time during the night, when that process or step may not be actively observed. This time interval is from about 8 to about 20 hours, or about 10-18 hours, typically about 16 hours.

As used herein, the term "reduced pressure" refers to a pressure that is less than atmospheric pressure. For example, a reduced pressure employed, for example in the context of drying conditions, is about 10 mbar to about 50 mbar, preferably 30-50 mbar.

As used herein, and unless indicated otherwise, the terms "wet crystalline form" or "wet form" refer to a polymorph that was not dried using any conventional techniques to remove residual solvent. Examples for such conventional techniques can be, but are not limited to, evaporation, vacuum drying, oven drying, drying under nitrogen flow, etc.

As used herein, and unless indicated otherwise, the terms "dry crystalline form" or "dry form" refer to a polymorph that was dried using any conventional techniques to remove residual solvent. Examples for such conventional techniques can be, but are not limited to, evaporation, vacuum drying, oven drying, drying under nitrogen flow, etc.

Figure 1:
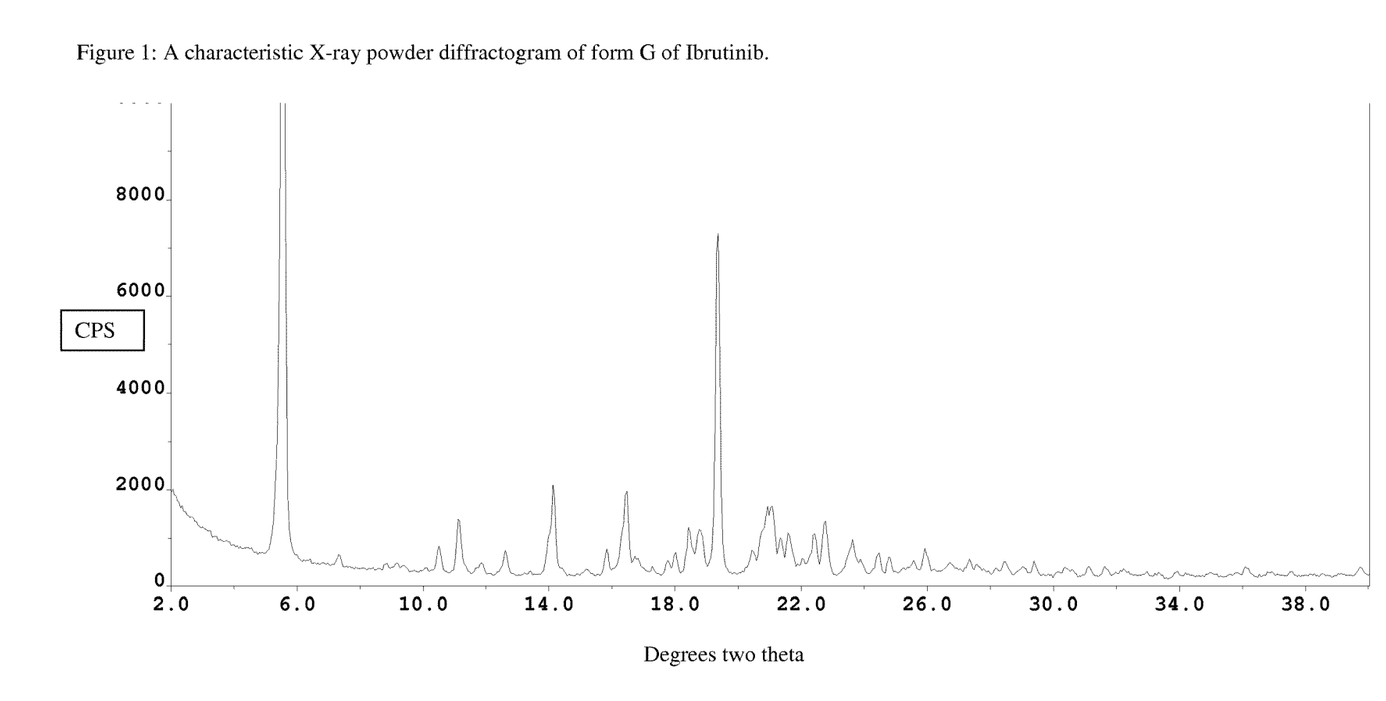
FIG. 1 shows an X-ray powder diffractogram of form G of Ibrutinib.

In one aspect, the present invention relates to a crystalline form of Ibrutinib, designated form G. Ibrutinib form G may be characterized by data selected from one or more of the following: an X-ray powder diffraction pattern having peaks at: 5.6, 10.6, 14.1, 16.5 and 19.4 degrees two theta±0.2 degrees two theta; an X-ray diffraction pattern having peaks at 12.6, 15.8, 16.5, 19.4 and 22.7 degrees 2-theta±0.2 degrees 2-theta; an X-ray powder diffraction pattern substantially as depicted in FIG. 1; or a combination of these data.

In some embodiments, crystalline form G of Ibrutinib may be characterized by X-ray powder diffraction pattern having peaks at: 5.6, 10.6, 14.1, 16.5 and 19.4 degrees 2-theta±0.2 degrees two theta and also having one, two, three, four or five peaks selected from: 12.6, 15.8, 21.1, 21.6 and 22.7 degrees 2-theta±0.2 degrees 2-theta.

In certain embodiments, crystalline form G of Ibrutinib may be characterized by X-ray powder diffraction pattern having peaks at 12.6, 15.8, 16.5, 19.4 and 22.7 degrees 2-theta±0.2 degrees 2-theta and also having one, two, three, four or five peaks selected from 5.6, 10.6, 14.1, 21.1 and 21.6 degrees 2-theta±0.2 degrees 2-theta.

In some embodiments, form G of Ibrutinib is isolated.

The above Ibrutinib form G may be obtained either as a wet form, or a dry form.

In some embodiments of this aspect of the present invention, the above form G may be a solvated form, preferably an acetic acid solvate.

With regard to the presence of solvents in a solid state form, it will be understood that the ultimate content/stoichiometric ratio will often depend on, inter alia, the drying conditions for the solid state form and also the strength of the interaction between the solvent and the compound molecules in the crystal. Thus, in some embodiments, the stoichiometry (molar ratio) of Ibrutinib to acetic acid may be between about 3:1 and about 6:1.

In another embodiment form G contains also water. Thus in some embodiments, the stoichiometry (molar ratio) of Ibrutinib:Acetic acid:$H_2O$ is between about 6:2:0 and about 6:1:6.

Figure 3:
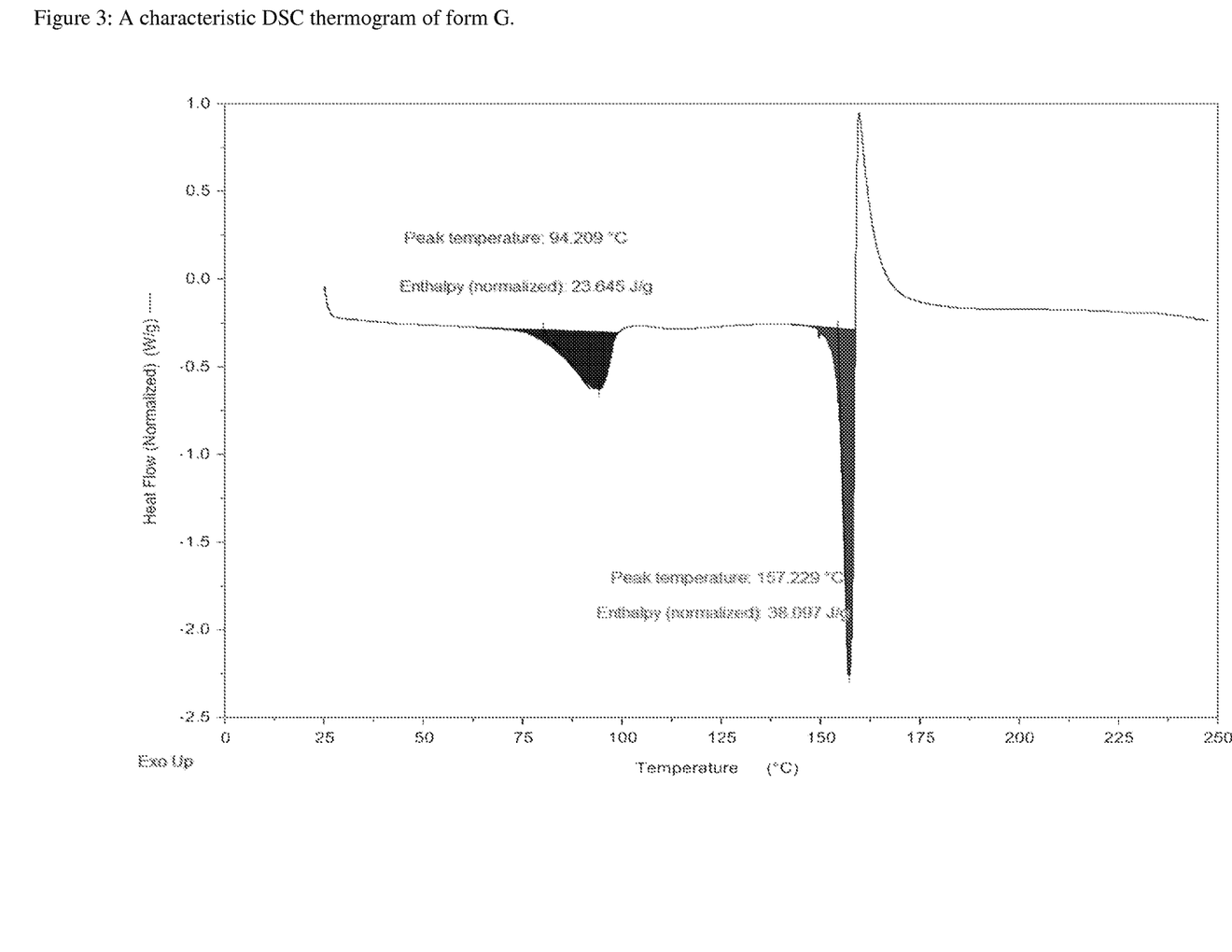
FIG. 3 shows an DSC thermogram of form G of Ibrutinib.

Ibrutinib form G may in certain embodiments be characterized, alternatively or in addition, by a characteristic DSC endotherm with $T_{peak}$ at 80-110° C., more specifically at 90-100° C., when scanning at 10°/min heating rate. A typical DSC thermogram of such an embodiment is depicted in FIG. 3.

Figure 4:
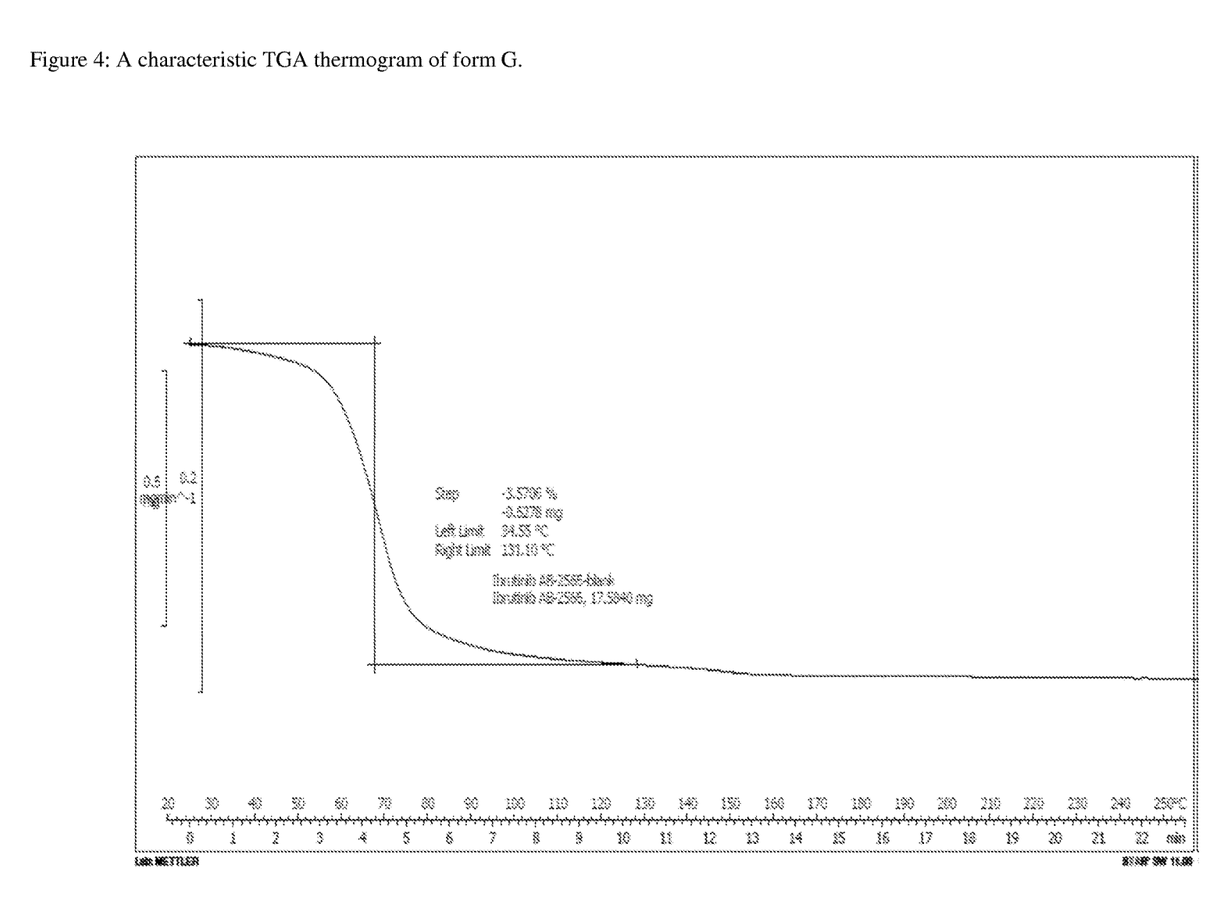
FIG. 4 shows a TGA thermogram of form G of Ibrunitib.

In other embodiments, Ibrutinib form G may be characterized, alternatively or in addition, by a TGA weight loss of between about 2.5-5.0%, more specifically at 3-4.5%. A representative TGA thermogram for such embodiments of Ibrutinib form G is depicted in FIG. 4.

As discussed above, crystalline form G may exhibit some advantages over other solid state forms of Ibrutinib, such as chemical purity, flowability, solubility, dissolution rate, morphology or crystal habit, stability-such as chemical stability as well as thermal and mechanical stability with respect to polymorphic conversion, stability towards dehydration and/or storage stability, low content of residual solvent, a lower degree of hygroscopicity, flowability, and advantageous processing and handling characteristics such as compressibility and bulk density. For example, Ibrutinib form G of the present invention can be obtained from crystallization with a very high purity. In particular, form G may be obtained with such a purity that none of the impurities/side products will be present at more than 1000 ppm. It has been found that other solid state forms of Ibrutinib, such as form A, may contain certain impurities at levels of more than 1000 ppm which cannot be removed by standard bulk methods (such as by simple crystallization).

Thus, in certain embodiments, Ibrutinib form G may be further defined by an overall purity (area % by HPLC) of at least about 99.5%, or even at least about 99.7%. Preferably, no single impurity will exceed about 0.1% (1000 ppm) in such embodiments.

In view of the high purity (achievable by simple crystallization), Ibrutinib form G not only qualifies as a suitable form to be used in pharmaceutical products, but may also be useful as a synthetic intermediate to reduce such unwanted impurities to acceptable levels.

Another aspect of the present invention relates to a process for preparing Ibrutinib form G. The process may comprise isolation of Ibrutinib form G from a reaction mixture or a solution of ibrutinib in acetic acid, preferably by the addition of water to induce precipitation. Ibrutinib form G may also be obtained from a solution of isopropanol/water to which a solution of Ibrutinib in acetic acid is slowly added. Alternatively, Ibrutinib form G may also be obtained from a solution of Ibrutinib in a mixture of acetonitrile, water, and acetic acid (40 mL) by cooling the solution and isolating the precipitated crystals form the mixture.

Figure 2:
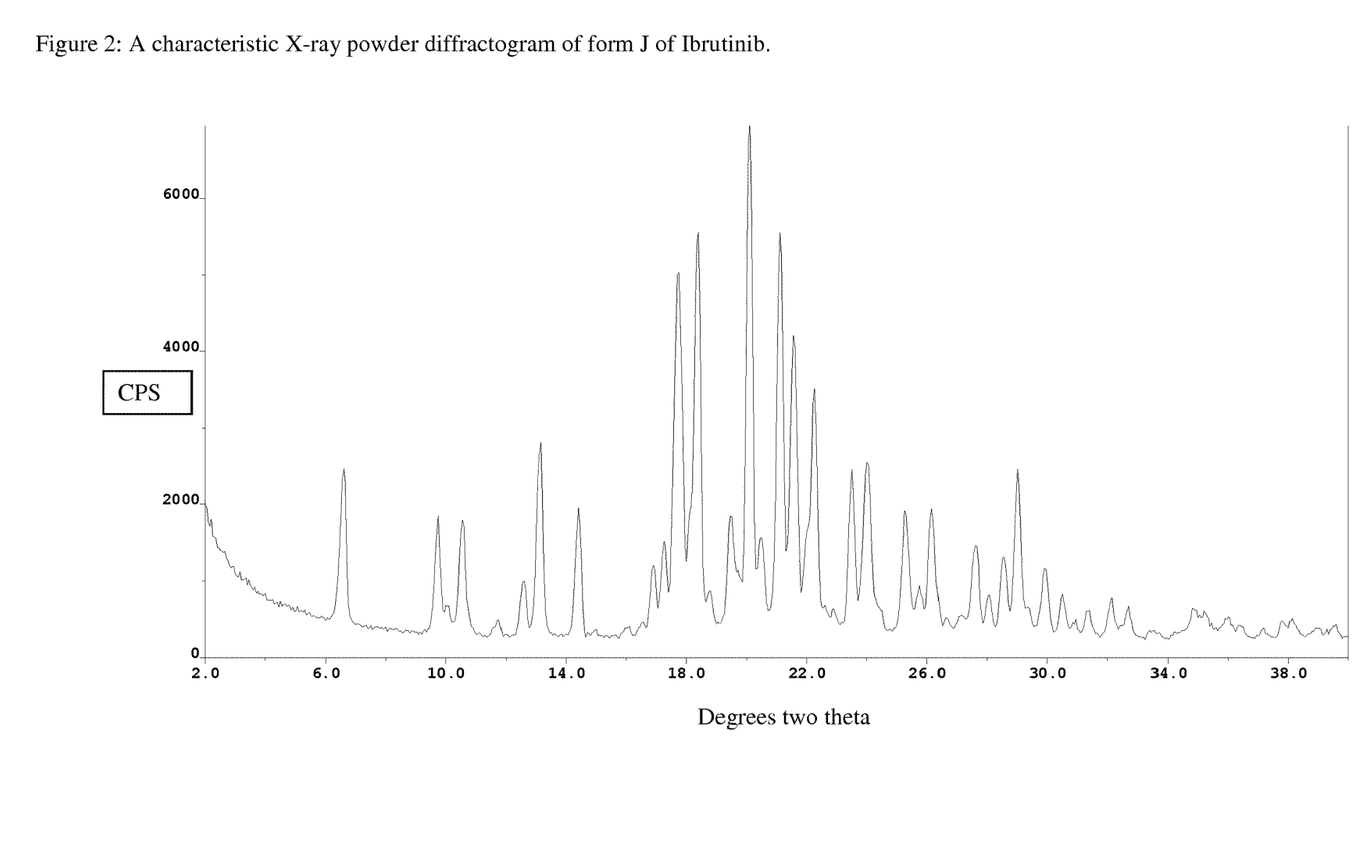
FIG. 2 shows an X-ray powder diffractogram of form J of Ibrutinib.

In another aspect, the present disclosure relates to a crystalline form of Ibrutinib designated as form J. Ibrutinib form J may be characterized by data selected from one or more of the following: X-ray powder diffraction pattern having peaks at 6.5, 9.7, 10.5, 13.0 and 14.3 degrees two theta±0.2 degrees two theta; an X-ray powder diffraction pattern as depicted in FIG. 2; or combinations of these data.

In some embodiments, crystalline form J of Ibrutinib may be characterized by an X-ray powder diffraction pattern having peaks at: 6.5, 9.7, 10.5, 13.0 and 14.3 degrees two theta±0.2 degrees two theta and also having one, two, three, four or five peaks selected from: 17.6, 18.3, 20.0, 21.0 and 21.5 degrees two theta±0.2 degrees two theta.

The above form J may in certain embodiments be a solvated form, preferably an Anisole solvate.

Figure 5:
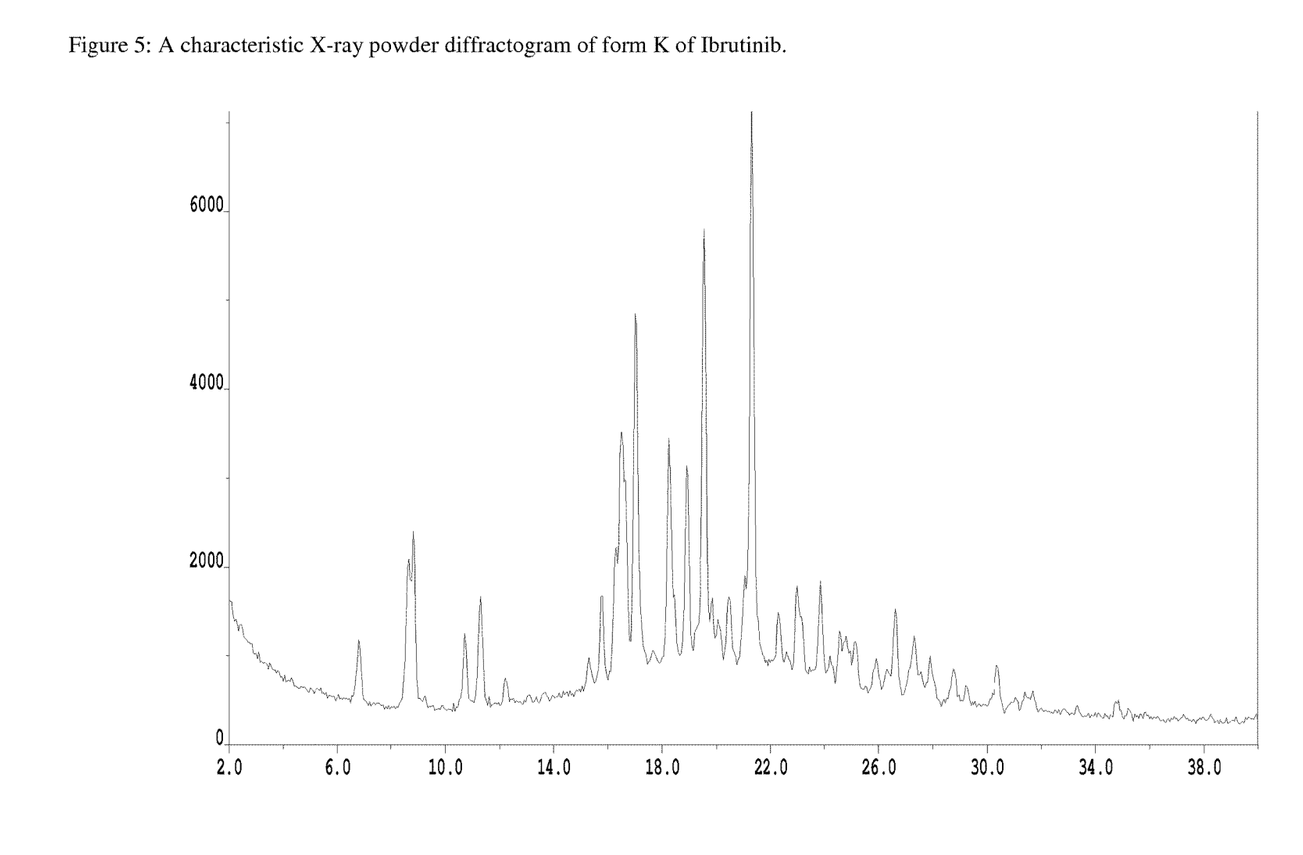
FIG. 5 shows an X-ray powder diffractogram of form K of Ibrutinib.

In another aspect, the present disclosure relates to a crystalline form of Ibrutinib designated as form K. Ibrutinib form K may be characterized by data selected from one or more of the following: X-ray powder diffraction pattern having peaks at 6.8, 11.3, 16.5, 17.0, and 23.0 degrees two theta±0.2 degrees two theta; an X-ray powder diffraction pattern as depicted in FIG. 5; or combinations of these data.

In some embodiments, crystalline form K of Ibrutinib may be characterized by an X-ray powder diffraction pattern having peaks at: 6.8, 11.3, 16.5, 17.0, and 23.0 degrees two theta±0.2 degrees two theta and also having one, two, three, four or five peaks selected from: 10.7, 15.8, 18.3, 18.9 and 23.8 degrees two theta±0.2 degrees two theta. The above described solid state forms of Ibrutinib can, inter alia, be used to prepare 1) other solid state forms of Ibrutinib; and 2) Ibrutinib salts and their solid state forms thereof.

The present invention further encompasses the use of crystalline Ibrutinib form G, form J or mixtures thereof in the preparation of pharmaceutical compositions or pharmaceutical formulations comprising ibrutinib as an active pharmaceutical ingredient.

The present invention also comprises pharmaceutical compositions comprising the crystalline Ibrutinib form G, form J or mixtures thereof. Typically, the pharmaceutical composition is a solid composition, and the Ibrutinib in the composition retains its solid state form.

Pharmaceutical formulations comprising the crystalline Ibrutinib form G, form J or mixtures thereof and at least one pharmaceutically acceptable excipient represent another aspect of the present invention. These pharmaceutical formulations can be prepared by a process comprising combining the crystalline forms of Ibrutinib of the present invention with at least one pharmaceutically acceptable excipient. Thus, the present invention further encompasses the use of the above-described crystalline forms of Ibrutinib in the manufacture of a pharmaceutical composition and/or a pharmaceutical formulation.

The above Ibrutinib crystalline forms G, J or mixtures thereof of the present invention can also be used in therapy, i.e. as a medicament, preferably for the treatment of cancer, such as B-cell lymphoma.

The present invention further encompasses a method of treating a subject suffering from cancer, such as B-cell lymphoma, or otherwise in need of the treatment, comprising administration of an effective amount of a pharmaceutical composition or formulation comprising the above crystalline forms of Ibrutinib described herein.

Having thus described the invention with reference to particular preferred embodiments and illustrative examples, those in the art can appreciate modifications to the invention as described and illustrated that do not depart from the spirit and scope of the invention as disclosed in the specification. The Examples are set forth to aid in understanding the invention but are not intended to, and should not be construed to limit its scope in any way.

X-Ray Powder Diffraction Method

The analysis was performed on an ARL (SCINTAG) powder X-Ray diffractometer model X'TRA equipped with a solid state detector. Copper-Kα radiation of 1.5418 Å was used. Scanning parameters: range: 2-40 degrees two-theta; scan mode: continuous scan; step size: 0.05°, and a rate of 3 deg/min.

DSC Method

DSC analysis was performed on a TA Discovery DSC instrument with the following experimental parameters:
Heating between 25° C.-250° C., heating rate: 10° C./min.
Sample weight: 3-5 mg.
Crucible: 40 μL aluminum T-zero pan with T-zero lid.
Purging with 50 ml/min $N_2$ flow.

TGA Method

TGA analysis was performed on a Mettler Toledo TGA/DSC 1 instrument with the following experimental parameters:
Heating between 25-250° C., heating rate: 10° C./min.
Sample weight: 7-15 mg.
Crucible: 150 μL alumina crucible.
Purging with 40 ml/min $N_2$ flow.

EXAMPLES

Reference Example

The starting Ibrutinib may be prepared according to the process described in U.S. Pat. No. 7,514,444, Example 1b (which follows Example 1a): 101 mg of 4-amino-3-(4-phenoxyphenyl)-1H-pyrazolo[3,4-d]pyrimidine and 330 mg of polymer-bound triphenylphosphine (TPP) (polymerlab) were mixed together with 5 mL of tetrahydrofuran (THF). tert-Butyl 3-hydroxypiperidine-1-carboxylate (200 mg; 2.0 equivalents) was added to the mixture followed by the addition of diisopropyl diazodicarboxylate (0.099 mL). The reaction mixture was stirred at room temperature overnight. The reaction mixture was filtered to remove the resins and the reaction mixture was concentrated and purified by flash chromatography (pentane/ethyl acetate=1/1) to give intermediate 3 (55 mg). Intermediate 3 (48.3 mg) was treated with 1 mL of 4N HCl in dioxane for 1 hour and then concentrated to dryness. The residue was dissolved in dichloromethane and triethylamine (0.042 mL) was added followed by acryl chloride (0.010 mL). The reaction was stopped after 2 hours. The reaction mixture washed with 5% by weight aqueous citric acid and then with brine. The organic layer was dried with $MgSO_4$, and concentrated, followed by purification using flash chromatography (with $CH_2Cl_2MeOH=25/1$).

Example 1: Preparation of Crystalline Form G of Ibrutinib

Ibrutinib (0.3 gr, amorphous form) was dissolved in acetic acid (1.2 ml) and the obtained solution was stirred at room temperature overnight followed by the addition of water (2.4 ml). A gum was obtained which was turned into cloudy solution upon stirring. The obtained cloudy solution was stirred for 9 days at room temperature and the obtained precipitate was collected by suction filtration. The obtained solid was dried in an oven at 40° C. under vacuum for 16 h to obtain form G of Ibrutinib (0.12 g), as confirmed by XRPD.

Example 2: Preparation of Crystalline Form 3 of Ibrutinib

Ibrutinib (5.2 g) was dissolved in Anisole (15 ml), the solution was stirred at room temperature until precipitation was occurred. The slurry was stirred over night at room temperature and the precipitate was collected by suction filtration. The cake was dried in a vacuum oven at 50° C. overnight. The obtained product was analyzed by XRPD and found to be form J.

Example 3: Preparation of Crystalline Form 3 of Ibrutinib

Ibrutinib (10.5 g) was dissolved in Anisole (21 ml) and MTBE (32 ml), the solution was stirred at room temperature until precipitation was occurred. The slurry was heated to reflux and was gradually cooled to room temperature. After 3 hours the precipitate was collected by suction filtration. The obtained product was analyzed by XRPD and found to be form J.

Example 4: Preparation of Crystalline Form G of Ibrutinib

A 1 L reactor was charged with Ibrutinib (100 g), acetonitrile (417.5 mL), water (417.5 mL) and acetic acid (27.15 g). The mixture was heated to 90° C. until dissolution; the solution was gradually cooled to 0° C., then heated to 25° C. and stirred over 48 hours at 25° C. The obtained slurry was filtered and washed with water (100 mL). The product was dried overnight in a vacuum oven at 40° C. to obtain Ibrutinib form G (72.9 g), as confirmed by XRPD.

Example 5: Preparation of Crystalline Form G of Ibrutinib

A 250 mL round flask was charged with isopropanol (10 mL) and water (120 mL), and a solution of Ibrutinib (10 g) in Acetic acid (40 mL) was added dropwise. The mixture was stirred at 25° C. for 48 hours. The obtained slurry was filtered and the wet product was slurried in water (50 mL) for 5 min and filtered again. The obtained product was dried under vacuum at room temp in the presence of a $N_2$ atmosphere and found to be form G, as confirmed by XRPD.

Example 6: Preparation of Crystalline Form K of Ibrutinib

Ibrutinib (10 g) was dissolved in toluene (50 mL) and dimethylformamide (DMA) (30 mL) at room temperature, the solution was heated to 50° C. and water (30 mL) was added. The phases were separated and methyl tert-butyl ether (MTBE) (30 mL) was added to the organic phase. The solution was cooled in an ice bath and seeded with amorphous Ibrutinib. After further stirring at the same temperature the obtained slurry was filtered under vacuum. The obtained solid was analyzed by XRPD and found to be Form K (FIG. 5).

What is claimed is:

1. A crystalline form of Ibrutinib designated as form G, characterized by data selected from one or more of the following: X-ray diffraction pattern having peaks at 5.6, 10.6, 14.1, 16.5 and 19.4 degrees 2-theta±0.2 degrees 2-theta; X-ray diffraction pattern having peaks at 12.6, 15.8, 16.5, 19.4 and 22.7 degrees 2-theta±0.2 degrees 2-theta; an X-ray powder diffraction pattern as depicted in FIG. 1; or combinations of these data.

2. A crystalline form of Ibrutinib designated as form G, characterized by an X-ray diffraction pattern having peaks at 5.6, 10.6, 14.1, 16.5 and 19.4 degrees 2-theta±0.2 degrees 2-theta, and further characterized by having one, two, three, four, or five additional peaks selected from: 12.6, 15.8, 21.1, 21.6 and 22.7 degrees 2-theta±0.2 degrees 2-theta.

3. A crystalline form of Ibrutinib designated as form G, characterized by an X-ray diffraction pattern having peaks at 12.6, 15.8, 16.5, 19.4 and 22.7 degrees 2-theta±0.2 degrees 2-theta and further characterized by having one, two, three, four, or five additional peaks selected from 5.6, 10.6, 14.1, 21.1 and 21.6 degrees 2-theta±0.2 degrees 2-theta.

4. The crystalline form G according to claim 1, wherein said form is a solvated form.

5. The crystalline form G according to claim 1, wherein form G is an acetic acid solvate.

6. The crystalline form G according to claim 5 wherein form G is also hydrated.

7. The crystalline form G according to claim 1, further characterized by a chemical purity of at least 99.5%.

8. A pharmaceutical formulation comprising Ibrutinib form G as defined in claim 1 and at least one pharmaceutically acceptable excipient.

9. A process for preparing other solid state forms of Ibrutinib, salts of Ibrutinib, and/or pharmaceutical compositions thereof, comprising preparing form G as defined in claim 1 and converting it to the desired solid state form or salt of Ibrutinib.

10. A process for preparing Ibrutinib form G as defined in claim 1, comprising obtaining a reaction mixture of ibrutinib in acetic acid and precipitating Ibrutinib form G.

11. The process of claim 10, wherein the reaction mixture comprises an organic solvent, water or mixture thereof.

12. A process for preparing the pharmaceutical formulation according to claim 8 comprising combining Ibrutinib form G as defined in claim 1, with at least one pharmaceutically acceptable excipient.

13. A method for treating cancer in a subject in need thereof, said method comprising the step of administering to said subject a therapeutically effective amount of Ibrutinib form G as defined in claim 1 or a pharmaceutical formulation thereof comprising the therapeutically effective amount Ibrutinib form G as defined in claim 1 and at least one pharmaceutically acceptable excipient.

14. The method for treating cancer according to claim 13, wherein said cancer is B-cell lymphoma.

* * * * *